(12) United States Patent
Fu et al.

(10) Patent No.: US 9,845,494 B2
(45) Date of Patent: Dec. 19, 2017

(54) ENZYMATIC METHODS FOR GENOTYPING ON ARRAYS

(75) Inventors: Glenn K. Fu, Dublin, CA (US); Keith W. Jones, Sunnyvale, CA (US)

(73) Assignee: Affymetrix, Inc., Carlsbad, CA (US)

(*) Notice: Subject to any disclaimer, the term of this patent is extended or adjusted under 35 U.S.C. 154(b) by 605 days.

(21) Appl. No.: 11/874,848

(22) Filed: Oct. 18, 2007

(65) Prior Publication Data

US 2008/0131894 A1     Jun. 5, 2008

Related U.S. Application Data

(60) Provisional application No. 60/862,020, filed on Oct. 18, 2006.

(51) Int. Cl.
*C12Q 1/68* (2006.01)

(52) U.S. Cl.
CPC .................................. *C12Q 1/6827* (2013.01)

(58) Field of Classification Search
None
See application file for complete search history.

(56) References Cited

U.S. PATENT DOCUMENTS

| | | | |
|---|---|---|---|
| 4,437,975 A | 3/1984 | Gillespie et al. |
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 4,988,617 A | 1/1991 | Landegren et al. |
| 5,143,854 A | 9/1992 | Pirrung et al. |
| 5,242,794 A | 9/1993 | Whiteley et al. |
| 5,252,743 A | 10/1993 | Barrett et al. |
| 5,324,633 A | 6/1994 | Fodor et al. |
| 5,333,675 A | 8/1994 | Mullis et al. |
| 5,384,261 A | 1/1995 | Winkler et al. |
| 5,405,783 A | 4/1995 | Pirrung et al. |
| 5,409,818 A | 4/1995 | Davey et al. |
| 5,412,087 A | 5/1995 | McGall et al. |
| 5,413,909 A | 5/1995 | Bassam et al. |
| 5,424,186 A | 6/1995 | Fodor et al. |
| 5,451,683 A | 9/1995 | Barrett et al. |

(Continued)

FOREIGN PATENT DOCUMENTS

| | | |
|---|---|---|
| WO | WO 88/10315 | 12/1988 |
| WO | WO 90/06995 | 6/1990 |

(Continued)

OTHER PUBLICATIONS

Nickerson et al., "Automated DNA diagnostics using ELISA-based oligonucleotide ligation assay," Proceedings of the National Academy of Sciences, USA, vol. 87, pp. 8923-8927, Nov. 1990.*

(Continued)

*Primary Examiner* — Joseph G Dauner
(74) *Attorney, Agent, or Firm* — Double Helix Law

(57) ABSTRACT

The invention relates to methods for enzymatic, genotyping of polymorphisms on solid supports. In some aspects the methods include ligation of allele or base specific interrogation probes to an array probe. The array probe is labeled by ligation of the interrogation probe. Ligation is dependent on the identity of the base immediately adjacent to the end of the array probe. In other aspects array bound probes are labeled by template dependent extension.

10 Claims, 9 Drawing Sheets

(56) References Cited

U.S. PATENT DOCUMENTS

| | | | |
|---|---|---|---|
| 5,474,796 A * | 12/1995 | Brennan | ............... 427/2.13 |
| 5,482,867 A | 1/1996 | Barrett et al. | |
| 5,491,074 A | 2/1996 | Aldwin et al. | |
| 5,494,810 A | 2/1996 | Barany et al. | |
| 5,527,681 A | 6/1996 | Holmes | |
| 5,541,061 A | 7/1996 | Fodor et al. | |
| 5,547,839 A | 8/1996 | Dower et al. | |
| 5,550,215 A | 8/1996 | Holmes | |
| 5,554,517 A | 9/1996 | Davey et al. | |
| 5,571,639 A | 11/1996 | Hubbell et al. | |
| 5,578,832 A | 11/1996 | Trulson et al. | |
| 5,593,839 A | 1/1997 | Hubbell et al. | |
| 5,599,695 A | 2/1997 | Pease et al. | |
| 5,624,711 A | 4/1997 | Sundberg et al. | |
| 5,631,734 A | 5/1997 | Stern et al. | |
| 5,733,729 A | 3/1998 | Lipshutz et al. | |
| 5,744,305 A | 4/1998 | Fodor et al. | |
| 5,795,716 A | 8/1998 | Chee | |
| 5,800,992 A | 9/1998 | Fodor et al. | |
| 5,831,070 A | 11/1998 | Pease et al. | |
| 5,834,758 A | 11/1998 | Trulson et al. | |
| 5,837,832 A | 11/1998 | Chee et al. | |
| 5,856,092 A | 1/1999 | Dale et al. | |
| 5,856,101 A | 1/1999 | Hubbell et al. | |
| 5,858,659 A | 1/1999 | Sapolsky et al. | |
| 5,861,245 A | 1/1999 | McClelland et al. | |
| 5,871,928 A | 2/1999 | Fodor et al. | |
| 5,874,219 A | 2/1999 | Rava et al. | |
| 5,889,165 A | 3/1999 | Fodor et al. | |
| 5,902,723 A | 5/1999 | Dower et al. | |
| 5,936,324 A | 8/1999 | Montagu | |
| 5,959,098 A | 9/1999 | Goldberg et al. | |
| 5,968,740 A | 10/1999 | Fodor et al. | |
| 5,974,164 A | 10/1999 | Chee | |
| 5,981,185 A | 11/1999 | Matson et al. | |
| 5,981,956 A | 11/1999 | Stern | |
| 6,013,449 A | 1/2000 | Hacia et al. | |
| 6,020,135 A | 2/2000 | Levine et al. | |
| 6,025,601 A | 2/2000 | Trulson et al. | |
| 6,033,860 A | 3/2000 | Lockhart et al. | |
| 6,040,138 A | 3/2000 | Lockhart et al. | |
| 6,040,193 A | 3/2000 | Winkler et al. | |
| 6,045,996 A * | 4/2000 | Cronin et al. | ............... 506/4 |
| 6,063,603 A | 5/2000 | Davey et al. | |
| 6,066,454 A | 5/2000 | Lipshutz et al. | |
| 6,090,555 A | 7/2000 | Fiekowsky et al. | |
| 6,136,269 A | 10/2000 | Winkler et al. | |
| 6,141,096 A | 10/2000 | Stern et al. | |
| 6,147,205 A | 11/2000 | McGall et al. | |
| 6,150,095 A * | 11/2000 | Southern | ............... B01J 19/0046 435/6.11 |
| 6,177,248 B1 | 1/2001 | Oliner et al. | |
| 6,185,030 B1 | 2/2001 | Overbeck | |
| 6,185,561 B1 | 2/2001 | Balaban et al. | |
| 6,188,783 B1 | 2/2001 | Balaban et al. | |
| 6,197,506 B1 | 3/2001 | Fodor et al. | |
| 6,201,639 B1 | 3/2001 | Overbeck | |
| 6,218,803 B1 | 4/2001 | Montagu et al. | |
| 6,223,127 B1 | 4/2001 | Berno | |
| 6,225,625 B1 | 5/2001 | Pirrung et al. | |
| 6,229,911 B1 | 5/2001 | Balaban et al. | |
| 6,262,216 B1 | 7/2001 | McGall | |
| 6,269,846 B1 | 8/2001 | Overbeck et al. | |
| 6,284,460 B1 | 9/2001 | Fodor et al. | |
| 6,287,778 B1 | 9/2001 | Huang et al. | |
| 6,300,063 B1 | 10/2001 | Lipshutz et al. | |
| 6,300,070 B1 | 10/2001 | Boles et al. | |
| 6,308,170 B1 | 10/2001 | Balaban | |
| 6,309,822 B1 | 10/2001 | Fodor et al. | |
| 6,310,189 B1 | 10/2001 | Fodor et al. | |
| 6,333,179 B1 | 12/2001 | Matsuzaki et al. | |
| 6,361,947 B1 | 3/2002 | Dong et al. | |
| 6,368,799 B1 | 4/2002 | Chee | |
| 6,386,749 B1 | 5/2002 | Watts et al. | |
| 6,391,592 B1 | 5/2002 | Su et al. | |
| 6,391,623 B1 | 5/2002 | Besemer et al. | |
| 6,410,276 B1 | 6/2002 | Burg et al. | |
| 6,428,752 B1 | 8/2002 | Montagu | |
| 6,582,908 B2 | 6/2003 | Fodor et al. | |
| 6,582,938 B1 | 6/2003 | Su et al. | |
| 6,632,611 B2 | 10/2003 | Su et al. | |
| 6,872,529 B2 | 3/2005 | Su | |
| 6,958,225 B2 | 10/2005 | Dong | |
| 7,097,976 B2 | 8/2006 | Kennedy | |
| 7,297,778 B2 | 11/2007 | Matsuzaki et al. | |
| 7,300,788 B2 | 11/2007 | Matsuzaki et al. | |
| 7,361,468 B2 | 4/2008 | Liu et al. | |
| 7,424,368 B2 | 9/2008 | Huang et al. | |
| 2001/0053519 A1 * | 12/2001 | Fodor | ............... B01J 19/0046 435/6.11 |
| 2003/0186279 A1 | 10/2003 | Kennedy et al. | |
| 2003/0186280 A1 | 10/2003 | Kennedy | |
| 2004/0012676 A1 | 1/2004 | Weiner et al. | |
| 2004/0072217 A1 | 4/2004 | Kennedy | |
| 2005/0227244 A1 | 10/2005 | Matsuzaki et al. | |
| 2005/0260628 A1 | 11/2005 | Matsuzaki et al. | |
| 2007/0065816 A1 | 3/2007 | Dong et al. | |

FOREIGN PATENT DOCUMENTS

| | | |
|---|---|---|
| WO | WO 99/36760 | 7/1999 |
| WO | WO 99/47964 | 9/1999 |
| WO | WO 00/58516 | 10/2000 |
| WO | WO 01/58593 | 8/2001 |
| WO | WO 2004/044225 | 5/2004 |

OTHER PUBLICATIONS

Merriam-Wenstyer Online Dictionary, 1928, Allele, accessed Jun. 13, 2008.*
"Viruses" (Wikipedia.com, accessed Nov. 24, 2012).*
"How many species of bacteria are there" (wisegeek.com; accessed Jan. 21, 2014).*
"Fungi," (Wikipedia.com; accessed Jun. 3, 2013).*
"Plant," (Wikipedia.com; accessed Mar. 8, 2013).*
"Mammal," (Wikipedia.com; accessed Sep. 22, 2011).*
"Murinae," (Wikipedia.com, accessed Mar. 18, 2013).*
"List of sequenced bacterial genomes" (Wikipedia.com; accessed Jan. 24, 2014).*
U.S. Appl. No. 09/513,300, filed Feb. 25, 2000, Gingeras.
U.S. Appl. No. 09/536,841, filed Mar. 27, 2000, Fan et al.
U.S. Appl. No. 09/916,135, filed Jul. 25, 2001, Matsuzaki et al.
U.S. Appl. No. 10/646,674, filed Aug. 21, 2003, Dong et al.
U.S. Appl. No. 60/453,930, filed Mar. 11, 2003, He et al.
U.S. Appl. No. 60/454,090, filed Mar. 11, 2003, Cao et al.
U.S. Appl. No. 60/456,206, filed Mar. 11, 2003, Kennedy.
U.S. Appl. No. 60/493,495, filed Aug. 8, 2003, Kaiser.
Barringer et al, Gene 89:117 (1990).
Carrasquillo et al, 2002, Nat Genet 32: 327-244.
Chee et al, 1996, Science 274: 610-614.
D, Schaid (2005) Ann Hum Genet. 70:116-30.
D, Schaid, Genetic Epidemiol., 27:348-364 (2004).
Dong et al, Genome Research 11, 1418 (2001).
Fan et al, 2002, Genomics 79:58-62.
Fan et al, 2000 Genome Research 10:853-860.
Guatelli et al. PNAS 87:1874(1990).
Gunderson et al, Genome Research 8:1142-53.
Hacia et al, 1999, Nat Genet 22:164-167.
Kennedy et al, (2003), Nat. Biotech. 21:1233-7.
Kwoh et al. et al., PNAS 86:1173 (1989).
Landegren et al, Science 241, 1077 (1988).
Liu et al, 2003, Bioinformatics, 19:2397-2403.
Maitra et al, Genome Research 14(5): 812-9 (2004).
Matsuzaki et al, (2004) Genome Research 14(3):414-425.
Matsuzaki et al, (2004) Nature Methods, vol. 1, 109-111.
Wang et al, 1998, Science 280: 1077-1082.
Wu and Wallace, Genomics 4, 560 (1989).

* cited by examiner

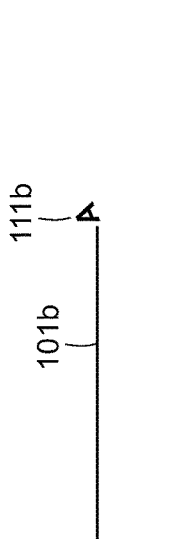
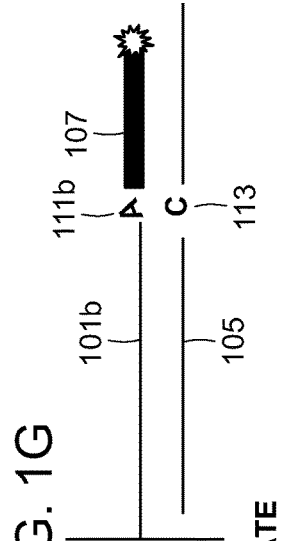
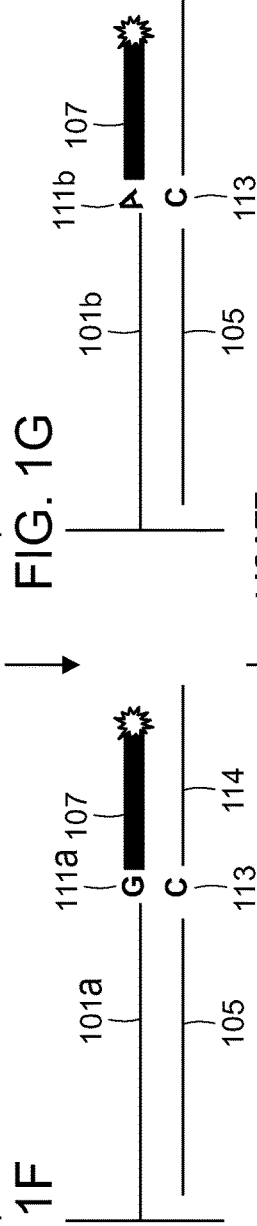
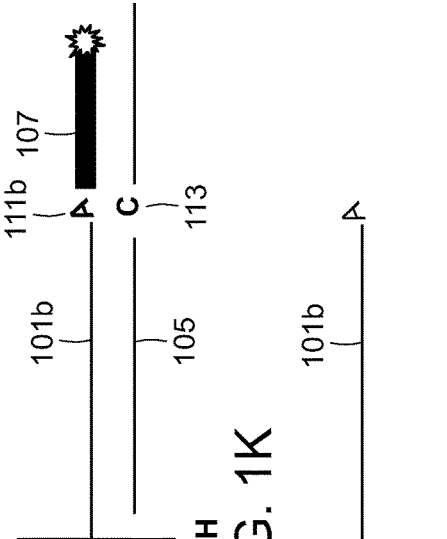
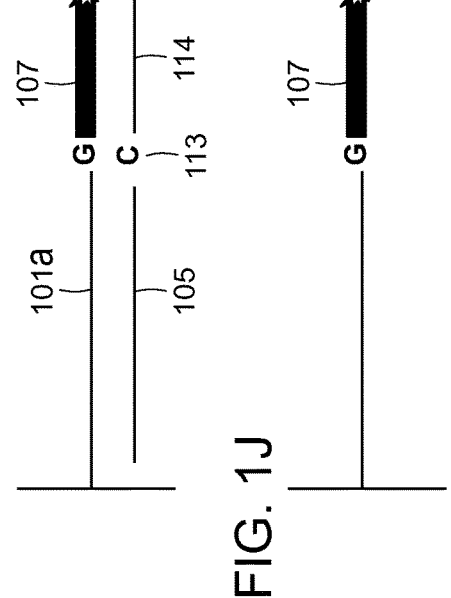

ASPE

SNP POSITION

SBE

SNP POSITION

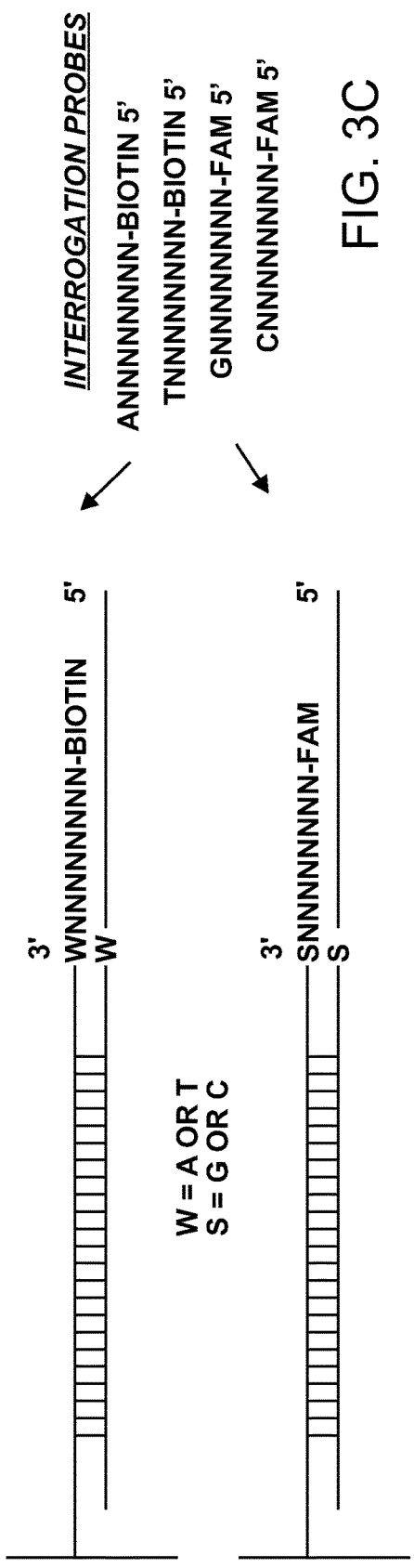

SEQUENCE LISTING

<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: Synthetic

<400> SEQUENCE: 1
ctacctcgtt tatcgatgta agctg                                    25

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2
gatggagcaa atagctacat tcgac                                    25

<210> SEQ ID NO 3
<211> LENGTH: 25
<212> TYPE: DNA
<213> ORGANISM: Artificial Sequence
<220> FEATURE:
<223> OTHER INFORMATION: Synthetic

<400> SEQUENCE: 3
ctacctcgtt tagcgatgta agctg                                    25

```
<210> SEQ ID NO 4
<211> LENGTH: 25
<212> TYPE: DNA
<213> ORGANISM: Artificial Sequence
<220> FEATURE:
<223> OTHER INFORMATION: Synthetic

<400> SEQUENCE: 4
gatggagcaa atcgctacat tcgac                                            25
```

ENZYMATIC METHODS FOR GENOTYPING ON ARRAYS

RELATED APPLICATIONS

The present application claims priority to U.S. application No. 60/862,020 filed Oct. 18, 2006, the disclosure of which is incorporated herein by reference in its entirety.

FIELD OF THE INVENTION

The present invention provides methods for genotyping using arrays of nucleic acid probes. The invention relates to diverse fields, including genetics, genomics, biology, population biology, medicine, and medical diagnostics.

BACKGROUND OF THE INVENTION

The past years have seen a dynamic change in the ability of science to comprehend vast amount of data. Pioneering technologies such as nucleic acid arrays allow scientists to delve into the world of genetics in far greater details than ever before. Exploration of genomic DNA has long been a dream of the scientific community. Held within the complex structures of genomic DNA lies the potential to identify, diagnose, or treat diseases like cancer, Alzheimer disease or alcoholism. Exploitation of genomic information from plants and animals may also provide answers to the world's food distribution problems.

Recent efforts in the scientific community, such as the publication of a haplotype map of the human genome, (IHMC, Nature 437, 1299-1320 (2005)), have changed the dream of genome exploration into a reality. Genome-wide assays, however, must contend with the complexity of genomes; the human genome for example is estimated to have a complexity of $3 \times 10^9$ base pairs. Because of their abundance, single nucleotide polymorphisms (SNPs) have emerged as the marker of choice for genome wide association studies and genetic linkage studies. High throughput methods for determining the genotypes of millions of SNPs in an individual will provide the framework for new studies to identify the underlying genetic basis of complex diseases such as cancer, mental illness and diabetes.

SUMMARY OF THE INVENTION

Methods for genotyping polymorphisms and particularly SNPs are disclosed. In preferred aspects the methods are enzymatic methods for marking probes bound to a solid support and thereby determining the identity of a polymorphic nucleotide.

In one aspect the methods include and array ligation step. The methods may be base specific ligation or allele specific ligation. In base specific ligation methods the unknown position is in the target and the probe on the array hybridizes so that the last base in the probe is adjacent to the unknown position. An interrogation probe with a 3' base that is complementary to the unknown position in the target hybridizes to the target to form a complex that includes the array probe, the interrogation probe and the template. In a preferred aspect interrogation probes are labeled according to the base at the 3' end of the probe-four different 3' bases so 4 different colors. In another aspect two colors are used.

In another aspect the ligation is allele specific and discrimination is based on the identity of the base at the end of the array probe. For a biallelic SNP there would be two probes for a given strand of a SNP, one for each allele. There may be two array probes for each strand. The interrogation probes may be random sequence and may all be labeled with a single label. Ligation of labeled interrogation probe to the array probe is an indication that the allele represented by that array probe is present.

In another aspect allele specific primer extension of array probes is disclosed. The extension may be single base extension where a single base corresponding to the SNP position is added and the identity of the base added is detected to determine the identity of the SNP allele. In another aspect allele specific primer extension is used.

The target to be hybridized to the array probes may be reduced in complexity, for example by WGSA or multiplex amplification methods or it may be whole genome or WGA product. The polymorphisms may be SNPs, insertions, deletions, copy number polymorphisms, or chromosomal rearrangements.

BRIEF DESCRIPTION OF THE FIGURES

FIG. 1D through FIG. 1K present a schematic sequence of steps for the allele specific ligation (ASL) in which the array probes include the interrogation position.

DETAILED DESCRIPTION OF THE INVENTION

Figure 1A:
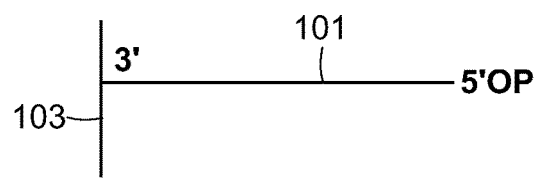
FIG. 1A through FIG. 1C present a schematic sequence of steps for the hybridization of a target to an array probe followed by ligation of an interrogation probe.

Reference will now be made in detail to exemplary embodiments of the invention. While the invention will be described in conjunction with the exemplary embodiments, it will be understood that they are not intended to limit the invention to these embodiments. On the contrary, the invention is intended to cover alternatives, modifications and equivalents, which may be included within the spirit and scope of the invention.

The invention therefore relates to diverse fields impacted by the nature of molecular interaction, including chemistry, biology, medicine and diagnostics. The ability to do so would be advantageous in settings in which large amounts of information are required quickly, such as in clinical diagnostic laboratories or in large-scale undertakings such as the Human Genome Project.

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited. All documents, i.e., publications and patent applications, cited in this disclosure, including the foregoing, are incorporated by reference herein in their entireties for all purposes to the same extent as if each of the individual documents were specifically and individually indicated to be so incorporated by reference herein in its entirety.

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (*Vols. I-IV*), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), Lehninger, *Principles of Biochemistry* 3$^{rd}$ Ed., W.H. Freeman Pub., New York, N.Y. and Berg et al. (2002) *Biochemistry*, 5$^{th}$ Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252, 743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication No. WO 99/36760) and PCT/US01/04285 (International Publication No. WO 01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Patent Application Publication No. 20070065816, and U.S. Pat. Nos. 6,872,529, 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, for example, *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. The sample may be amplified on the array. See, for example, U.S. Pat. No. 6,300,070 and U.S. Ser. No. 09/513, 300, which are incorporated herein by reference.

Other suitable amplification methods include the ligase chain reaction (LCR) (for example, Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA,* 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 6,582,938, 5,242,794, 5,494, 810, 4,988,617, each of which is incorporated herein by reference.

Additional methods of sample preparation and techniques for reducing the complexity of a nucleic sample are described in Dong et al., Genome Research 11, 1418 (2001), in U.S. Pat. Nos. 6,361,947, 6,391,592, 6,632,611, 6,958,225 and 6,872,529 and U.S. Ser. Nos. 09/916,135.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* (2$^{nd}$ Ed. Cold Spring Harbor, N.Y., 1989); Berger and Kimmel *Methods in Enzymology*, Vol. 152, *Guide to Molecular Cloning Techniques* (Academic Press, Inc., San Diego, Calif., 1987); Young and Davism, *P.N.A.S*, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Ser. No. 10/389,194 (U.S. Patent Application Publication 20040012676), 60/493,495 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., 2$^{nd}$ ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. Ser. No. 10/197,621 (U.S. Patent Application Publication 20030097222), Ser. No. 10/063,559 (United States Publication No. 20020183936), Ser. No. 10/065,856 (U.S. Patent Application Publication 20030100995), Ser. No. 10/065,868 (U.S. Patent Application Publication 20030120432), Ser. No. 10/328,818 (U.S. Patent Application Publication 20040002818), Ser. No. 10/328,872 (U.S. Patent Application Publication 20040126840), Ser. No. 10/423,403 (U.S. Patent Application Publication 20040049354), and 60/482,389.

A. Definitions

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to resin beads, silica chips, or other solid supports.

The term "biomonomer" as used herein refers to a single unit of biopolymer, which can be linked with the same or other biomonomers to form a biopolymer (for example, a single amino acid or nucleotide with two linking groups one or both of which may have removable protecting groups) or a single unit which is not part of a biopolymer. Thus, for example, a nucleotide is a biomonomer within an oligonucleotide biopolymer, and an amino acid is a biomonomer within a protein or peptide biopolymer; avidin, biotin, antibodies, antibody fragments, etc., for example, are also biomonomers.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "genotyping" refers to the determination of the genetic information an individual carries at one or more positions in the genome. For example, genotyping may comprise the determination of which allele or alleles an individual carries for a single SNP or the determination of which allele or alleles an individual carries for a plurality of SNPs. For example, a particular nucleotide in a genome may be an A in some individuals and a C in other individuals. Those individuals who have an A at the position have the A allele and those who have a C have the C allele. In a diploid organism the individual will have two copies of the sequence containing the polymorphic position so the individual may have an A allele and a C allele or alternatively two copies of the A allele or two copies of the C allele. Those individuals who have two copies of the C allele are homozygous for the C allele, those individuals who have two copies of the A allele are homozygous for the C allele, and those individuals who have one copy of each allele are heterozygous. The array may be designed to distinguish between each of these three possible outcomes. A polymorphic location may have two or more possible alleles and the array may be designed to distinguish between all possible combinations.

The term "label" as used herein refers to a luminescent label, a light scattering label or a radioactive label. Fluorescent labels include, inter alia, the commercially available fluorescein phosphoramidites such as Fluoreprime (Pharmacia), Fluoredite (Millipore) and FAM (ABI). See U.S. Pat. No. 6,287,778.

For a discussion of methods for using SNPs to test associations of SNPs and haplotypes with complex traits see, for example, D. Schaid (2005) Ann Hum Genet. 70:116-30 and D. Schaid Genetic Epidemiol. 27:348-364 (2004). Examples of mapping arrays include the Affymetrix Mapping 10K, Mapping 100K and Mapping 500K arrays and array sets. These mapping arrays are a type of genotyping array because the output is the genotype of a plurality of polymorphisms. Mapping arrays are also described, for example, in U.S. Pat. Nos. 7,361,468 and 7,300,788, and US Patent Publication No. 2005022724. Methods of using mapping arrays are also disclosed in Matsuzaki et al., Nat Methods 1: 109-11 (2004).

The term "oligonucleotide" or sometimes refer by "polynucleotide" as used herein refers to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "polymorphism" as used herein refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wild type form. Diploid organisms may be homozygous or heterozygous for allelic forms. A diallelic polymorphism has two forms. A triallelic polymorphism has three forms. Single nucleotide polymorphisms (SNPs) are included in polymorphisms. Single nucleotide polymorphisms (SNPs) are positions at which two alternative bases occur at appreciable frequency (>1%) in a given population. SNPs are the most common type of human genetic variation. A polymorphic site is frequently preceded by and followed by highly conserved sequences (e.g., sequences that vary in less than $\frac{1}{100}$ or $\frac{1}{1000}$ members of the populations).

A SNP may arise due to substitution of one nucleotide for another at the polymorphic site. A transition is the replacement of one purine by another purine or one pyrimidine by another pyrimidine. A transversion is the replacement of a purine by a pyrimidine or vice versa. SNPs can also arise from a deletion of a nucleotide or an insertion of a nucleotide relative to a reference allele.

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (for example, opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

The term "WGSA (Whole Genome Sampling Assay) Genotyping Technology" refers to a technology that allows the genotyping of thousands of SNPs simultaneously in complex DNA without the use of locus-specific primers. WGSA reduces the complexity of a nucleic acid sample by amplifying a subset of the fragments in the sample. In this technique, a nucleic acid sample is fragmented with one or more restriction enzyme of interest and adaptors are ligated to the digested fragments. A single primer that is complementary of the adaptor sequence is used to amplify fragments of a desired size, for example, 400-800, 400-2000 bps, using PCR. Fragments that are outside the selected size range are not efficiently amplified. The processed target is then hybridized to nucleic acid arrays comprising SNP-containing fragments/probes. WGSA is disclosed in, for example, U.S. Provisional Application Ser. No. 60/453,930 (now inactive), 60/454,090 (now inactive) and 60/456,206 (now inactive), in U.S. Pat. No. 7,424,368 (also PCT Application published as WO04/044225), U.S. Pat. Nos. 7,097,976 and 7,297,778, U.S. patent application Ser. No. 10/681,773 (U.S. Patent Application Publication No 20040146890), Ser. Nos. 10/646,674, 10/316,517 (U.S. Patent Application Publication 20030186279), Ser. Nos. 10/316,629, 10/463,991 (U.S. Patent Application Publication 20040072217), and Ser. No. 10/442,021 (U.S. Patent Application Publication 20070065816), each of which is hereby incorporated by reference in its entirety for all purposes.

Biochemical Assays for Genotyping Using Arrays

The millions of SNPs that have been identified in the human genome provide a large repository of markers for human variation, allowing construction of increasingly dense SNP maps and tools for analysis of large numbers of individual SNP markers. These tools have the potential of enabling investigators to generate high resolution mapping of complex human genetic traits, to understand the history of human populations, and to examine genomic abnormalities, such as chromosomal copy number changes that lead to cancer and other diseases.

Recent estimates suggest that there may be ~5 million SNPs with minor allele frequencies of at least 10%, and possibly as many as ~11 million with minor allele frequencies of at least 1% (Kruglyak and Nickerson, 2001, *Nat Genet.* 27: 234-236). Millions of human SNPs have been catalogued, many of which are publicly available in databases such as the TSC and NCBI dbSNP repositories (Thorisson and Stein, 2003, *Nucleic Acids Res* 31: 124-127).

To obtain the most comprehensive genotype information about an individual a study may determine the genotype of all 11 million known SNPs. This would be costly and time consuming given current technologies and not required for many research questions. Instead, researchers can take advantage of the tendency of regions of the genome to travel together as blocks representing regions of high linkage disequilibrium (LD). See, for example, Conrad et al., Nat. Genet. 38, 1251-1260 (2006). Because of LD it is possible to use a subset of SNPs that are characteristic of blocks of SNPs. The underlying assumption is that if a set of 5-10 SNPs is in high LD the genotype of one or two can be used as a surrogate to predict the genotype of the others. LD patterns however, vary across the human genome with some regions showing high LD with other regions showing low LD. LD also varies within populations so assumptions based on information obtained from one group of individuals may not be correct for another set of individuals. Methods for selecting an optimized set of SNPs to be used as fixed marker sets in whole-genome association studies are disclosed herein. Weight is given to marker spacing, allele frequency and the ability of a given genotyping assay to accurately and reproducibly make genotyping calls for the selected SNPs.

High density oligonucleotide arrays have been used to investigate polymorphisms (Chee et al., 1996, Science 274: 610-614.), and have been applied to SNP genotyping and mutation detection (Carrasquillo et al., 2002, Nat Genet. 32: 237-244; Fan et al., 2000 Genome Res 10: 853-860; Fan et al., 2002, Genomics 79: 58-62; Hacia et al., 1999, Nat Genet. 22: 164-167; Wang et al., 1998, Science 280: 1077-1082; Liu et al., 2003, Bioinformatics, 19: 2397-2403). Methods for performing ligation to probes bound to solid supports have been disclosed, for example, in Gunderson et al., Genome Res., 8:1142-53 (1998). The Affymetrix Mapping 500K array provides for simultaneous genotyping of more than 500,000 human SNPs and similar products in the future will allow genotyping of more than 1,000,000 SNPs.

Given the millions of SNPs that are estimated to exist and the large subset already in databases, there is a need to prune this number down to a number that will fit on a few microarrays at current feature sizes. Applications of microarray for SNP genotyping have been described in e.g., a number of U.S. patents and patent applications, including U.S. Pat. Nos. 6,300,063, 6,361,947, 6,368,799, 7,297,778 and 7,097,976, U.S. patent application Ser. No. 11/075,121 (U.S. Patent Application Publication No. 20050260628), and Ser. No. 10/442,021 (U.S. Patent Application Publication No. 2007065816) and US Patent Publication Nos. 20030186279, and 20030186280, all incorporated herein by reference in their entireties for all purposes. Methods and arrays for simultaneous genotyping of more than 10,000 and more than 100,000 SNPs have also been described for example in Kennedy et al., (2003) Nat. Biotech. 21:1233-7, Matsuzaki et al., (2004) Genome Res. 14(3): 414-425, and Matsuzaki et al., (2004) Nature Methods, Vol 1, 109-111, all incorporated herein by reference in their entireties for all purposes.

Methods for genotyping polymorphisms using arrays of oligonucleotide probes are disclosed. In preferred aspects the methods are on-array enzyme bases assays using primer extension and ligation. In some aspects DNA polymerase capable of using arrays probes as primers for extension is used. Methods are disclosed for reducing background resulting, for example, from self-priming and truncated probes. Methods that use array ligation are only minimally impacted by truncation or self-ligated probes. In some aspects high complexity DNA is hybridized to an array, including whole genome hybridization to a single array. In some aspects enzyme function is used to increase base discrimination instead of or in addition to discrimination through differential hybridization kinetics. The methods allow fewer probes for interrogation of each SNP as compared to methods that rely entirely on hybridization discrimination.

Methods are disclosed for genotyping using ligation of an interrogation probe to a target specific probe attached to an array. Ligation is template dependent and depends on the base present in the target and the base present at an interrogation position. The interrogation position may be at either the 5' end of the array probe or the 3' end of the interrogation probe. If the interrogation position is complementary to the polymorphic position in the target then ligation of the array probe to the interrogation probe takes place. In preferred aspects the interrogation probe is labeled with a detectable label. Ligation of the interrogation probe to the array probe results in covalent attachment of the interrogation probe to the solid support via the array probe. A high stringency wash may be performed to remove any nucleic acid that is not attached covalently to the solid support. Detection of labeled array probes may then be used to determine the genotype of polymorphisms in the target.

In one aspect the interrogation position is the 5' end of the array probe. Each allele of each polymorphism has a different sequence array probe, preferably separated into different features of the array. For example, if the polymorphism is a SNP two array probes that vary at the base at the 5' end of the probe are used to interrogate each strand (four different array probes if both strands are to be interrogated). Specificity of ligation is conferred by the presence of absence of complementarity between the polymorphic position and the 5' end of the array probe. The interrogation probe mixture may be a mixture of all possible sequences of a given length, for example, all possible 8 mers or all possible 9 mers.

In one aspect an Array Ligation Assay (ALA) is used for genotyping. Array Ligation Assay (ALA) is an on-array assay based on ligation. The methods allow for whole genome hybridization without complexity reduction. Enzyme function is used for base discrimination instead of allele specific hybridization. Each SNP requires as few as one or two features. For ALA the probes of the array may be in a 3' to 5' orientation, with the 3' end of the probe attached to the array leaving the 5' end of the probe available for ligation.

In one embodiment of ALA allele-specific ligation (ASL) is used to identify the base. ALA is shown schematically in FIG. 1A. The array probe 101 is attached to the solid support 103 at the 3' end of the probe. The array probe is complementary to the region to be genotyped. In preferred aspects the array probe 101 is 25 bases in length and the 5' end of the probe is phosphorylated. Preferably, only full length probes are phosphorylated. Unlabeled genomic DNA is fragmented and the fragments are hybridized to the array. The whole genome without complexity reduction may be hybridized to the array. A genomic fragment 105 that is complementary to probe 101 is shown hybridized to probe 101. An interrogation probe 107 with a 5' label 109 is hybridized to the DNA target 105 on the array.

Figure 1B:
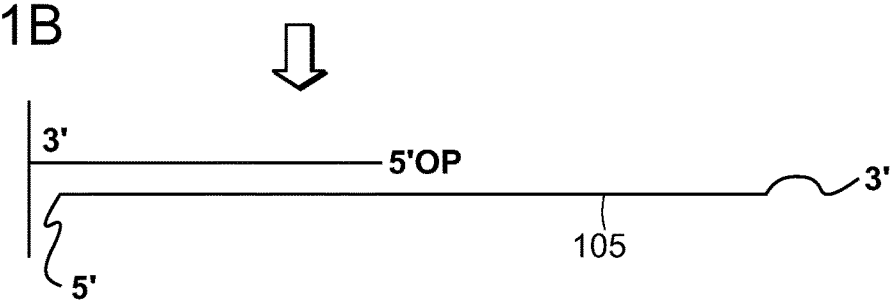

In one embodiment, shown in FIG. 1B, there are two array probes 101a and 101b that differ only in the SNP position 111a and 111b at the 5' end. The base at discrimination position 111 in the array probe 101 is complementary to one of the polymorphic alleles 113. In this embodiment the polymorphism is a SNP and position 111 is the discrimination position in the array probe. Depending on which allele or alleles is present the discrimination position is either complementary to the SNP in the target 113 or not. If 111 is complementary to the SNP allele at 113 the interrogation probe 117 and the probe SNP position 111 are juxtaposed and ligation takes place. If the SNP position in the probe is not complementary to the SNP position in the target 113 the interrogation probe still can hybridize but the SNP position in the probe is not juxtaposed with the 5' end of the interrogation probe 107 and ligation does not take place above background levels. For each allele of the SNP a different array probe is used 101a and 101b differing at the identity of the base 111a and 111b at the 5' end of the probe. The labeled interrogation probe 107 is ligated to the array probe 101a that is perfectly complementary to the target 105 including the SNP allele 113 present in the target. SNP position 111b is not complementary to 113 so the interrogation probe does not ligate to array probe 101b. The mismatch at the 5' end of the probe prevents ligation. For each SNP there are at least two array probes. If both strands of the DNA are to be interrogated each strand will be interrogated by two array probes.

The base 114 that is immediately 3' of the polymorphic position 113 in the target is preferably not polymorphic and is preferably of known sequence. The 3' end of the interrogation probe is complementary to this base and in one aspect interrogation probes that share the same 3' base are labeled with a detectable label. Each of the 4 types of interrogation probes may be labeled with a different label in addition to a common label. The different labels may be used to determine the level of non-specific signal and the level of the common label may be normalized to account for the non-specific signal. For example, all the probes may be labeled with DIG and each type labeled with one of the following: DNP, FI, biotin, dansyl. The DIG may be used for quantitation and the other 4 to measure non-specific signal. The signal from DIG should correspond to the signal from the label of the expected interrogation probe. If the base that is 3' of the SNP position is G then only interrogation probes terminating in a 3° C. should ligate. If interrogation probes with a 3° C. are labeled with Dansyl the amount of DIG and the amount of Dansyl should be proportional.

Figure 1C:
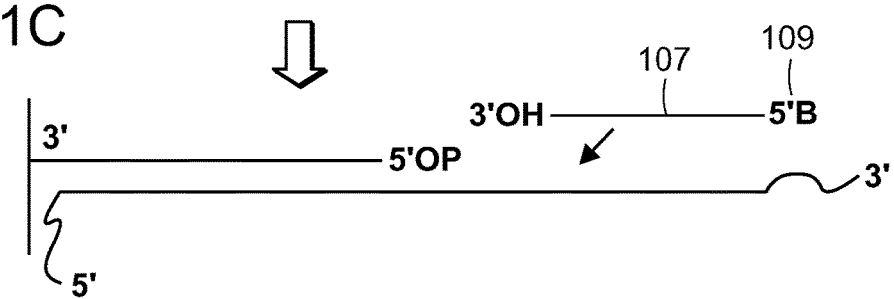
Figure 1N:
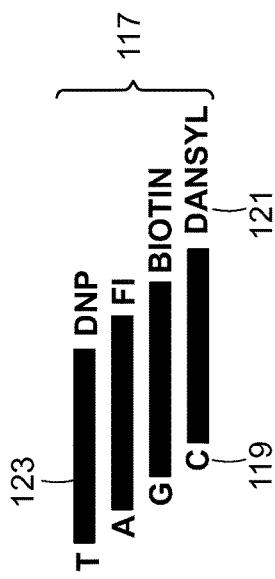
FIG. 1L through FIG. 1N present a schematic sequence of steps for the base specific ligation (BSL) in which the 3' position of the interrogation probe is the interrogation position.
Figure 1L:
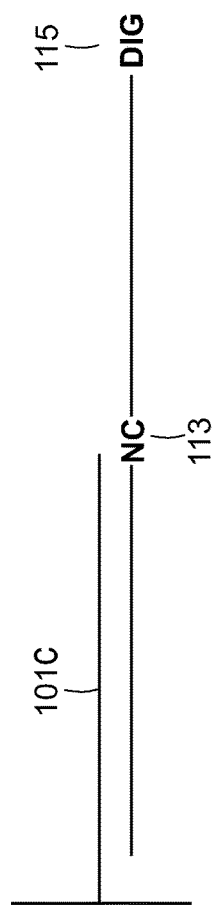
Figure 1M:
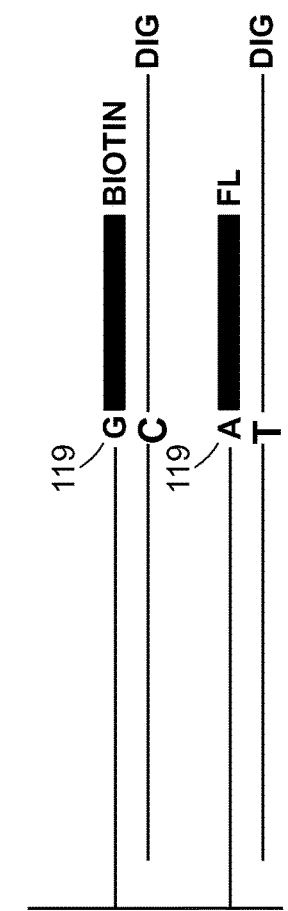

In another embodiment of ALA, shown in FIG. 1C, base-specific ligation (BSL) is used to identify the base. In this embodiment, the array probe terminates one base 5' of the SNP position 113. The array probe 111c terminates so that the last base is complementary to the base that is immediately 5' of the SNP position 113 in the target. The target may include a label 115. The label on the target may be used, for example, for quantitation. The interrogation probes 117 are labeled in a manner that is specific for the base present at the 3' end of the interrogation probe. There are four differentially detectable probes, corresponding to each of the four possible 3' bases. For example, all interrogation probes that have a 3' T are labeled with DNP, all that have 3' A are labeled with FI, all that have 3' G are labeled with biotin and all that have 3° C. are labeled with Dansyl. The central region 123 is preferably random, for example, $N_{5-8}$. The pool 117 of interrogation probes may be a pool of random hexamers varying in the label present at the 5' end. For each SNP a single array probe is used and the interrogation probes are ligated in an allele specific manner.

In another aspect BSL can be performed using two colors. For example, if the interrogation probes that end with T and A are labeled with biotin and the interrogation probes that end with G and C are labeled with DNP. Biallelic SNPs that are T/C, T/G, A/C or A/G can be distinguished using these interrogation probes, however, G/C and A/T SNPs would require a different approach. In some aspects the target may be labeled with another label, such as DIG, and this may be used for signal normalization.

Figure 2A:
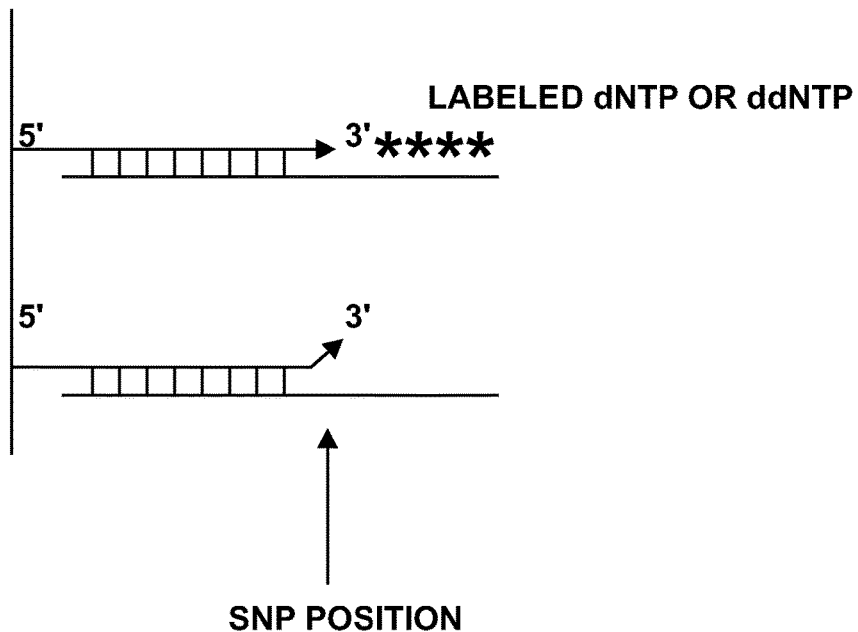
FIG. 2 is a schematic of the arrayed primer extension assay (APEX) in which the array probes are extended in a template dependent manner to determine the genotype of the target sequence. Allele specific primer extension (ASPE) is shown in 2A. Single base extension (SBE) is shown in 2B.
Figure 2B:
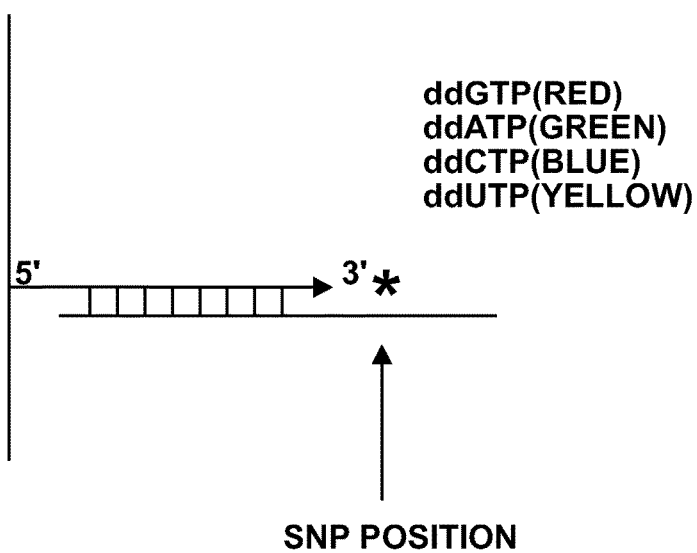

In another aspect primer extension is used for genotyping on an array. Arrayed Primer Extension Assay (APEX) is an on-array assay based on primer extension (shown in FIG. 2). The probes are attached to the array at the 5' end leaving the 3' end free for extension. In one aspect, shown in FIG. 2A, allele-specific probes are used and allele-specific primer extension (ASPE) is used. The extension may be a single base or multiple bases. The probe is designed so the SNP position is complementary to the base at the 3' end of the probe. This method uses two probes per SNP per strand or 4 per SNP. In another aspect, shown in FIG. 2B, single base extension (SBE) is used and the first based extended beyond the probe is identified. The probe is designed so the SNP position is 1 base beyond where the probe hybridizes (immediately adjacent to the 3' end of the probe). This method uses a single probe per SNP per strand. The labeled bases are indicated by *.

Because APEX methods include template mediated extension of the probe on the array, priming that is independent of specific template is a possibility. This may result from a probe folding back on itself, two neighboring probes interacting so that one probe uses the other as template for extension, or other non-specific interactions. Steps may be taken to reduce the amount of non-specific extension. For example, the temperature of the reaction may be elevated from 37° C. to 50° C., a denaturant like DMSO may be added at 0.1 to 10%, the PCR may be performed under Hot Start conditions so the reaction starts and ends at temperatures at or above 50° C., single-stranded binding proteins may be added, such as T4 gene32 and E. coli SSB, the level of magnesium can be titrated from about 0 to about 3.5 mM, spermidine can be added at about 0.1 to 2.5 mM, Na Pyrophosphate may be added at about 0.5 to 12.5 mM, or the enzyme to ddNTP concentration may be varied.

In some aspects the length of the interrogation probe may be varied. The effects of different interrogation probe lengths from 6 (N5g) to 9 (N8g) were tested. All interrogation probes were labeled with 5' biotin. Arrays were synthesized with either NNPOC/LDS or NNPOC/BisB. The results indicate that the arrays synthesized using LDS were better than those synthesized using BisB. Innosine was tested (I5G, I8 and I10) but failed to give good results. The best results were observed with a nonomer interrogation probe. Hybridization results are shown for N5G, N6G, N7G and N8G (fixed 3' G base) for either LDS (top row) or BisB (bottom row). Wobble base interrogation probes N9, N10, and N12 were also tested. T4 DNA ligase was compared to E. coli DNA ligase with either N8N or N8G. The E. coli DNA ligase gives less background and higher specificity. BSL using N8G was found to correctly discriminate and ligate the N8G to the array when the next base in the hybridized target is a C using either PCR product or whole genome as target. The labeled target hybridization patterns and the N8N hybridization pattern are shown as controls. In some aspects ALA reactions may also include N9 3' phosphate as a non-specific competitor for ligation.

In preferred aspects the APEX assay is optimized by reduction of the effect of truncated probes. This may be accomplished by increasing the step-wise yield efficiency of synthesis, for example, by photo acid generator synthesis methods; inactivation of non-full length probes, and use of an algorithm to subtract signal predicted from truncated probes. In another aspects effects of non-template dependent extension are minimized. This may be by optimization of reaction conditions; increase primer extension temperature by increasing probe length (5' to 3' VPL PAC chemistry to make 19-43 mers in 113 steps). Modified array chemistry can be used to eliminate self-extension template for DNA polymerase, such as phosphorothioate linkages. In some aspects a computer may be used to predict and avoid sequences with propensity for hairpins.

Figure 3D:
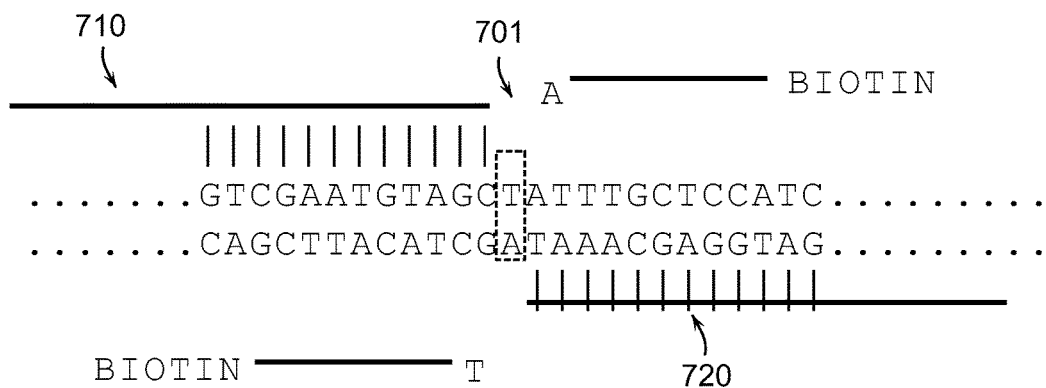
FIG. 3 shows a method for genotyping biallelic SNPs using two different labels.
Figure 3E:
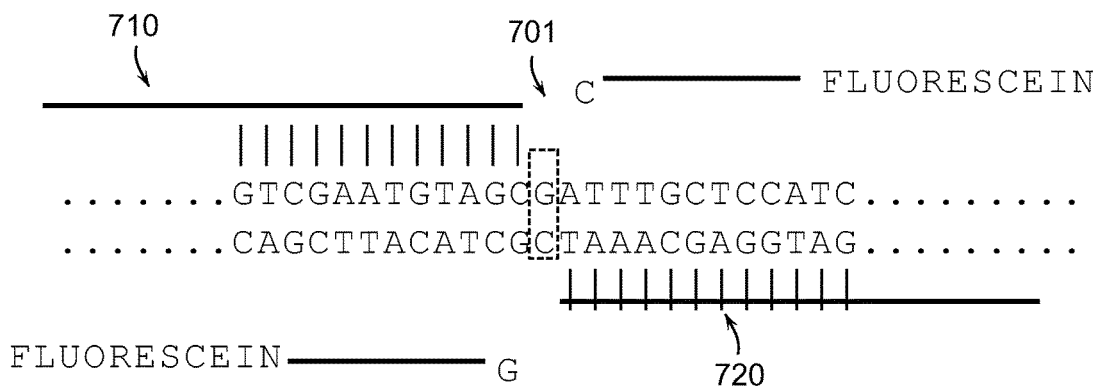
Figure 4A:
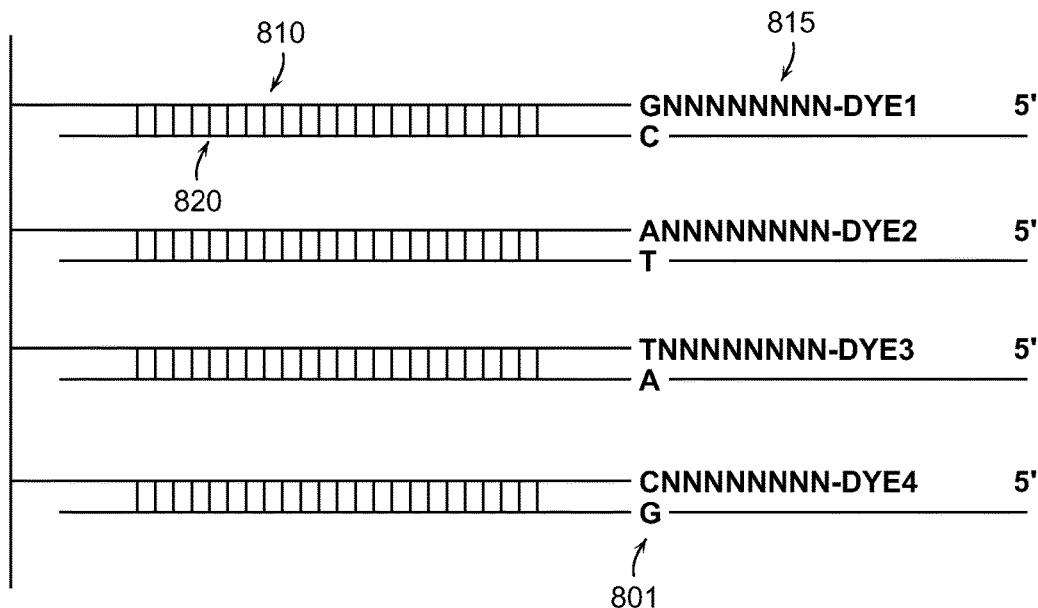
FIG. 4 shows a method for identifying multiple based in a target using ligation followed by cleavage and subsequent rounds of ligation and cleavage.
Figure 4B:
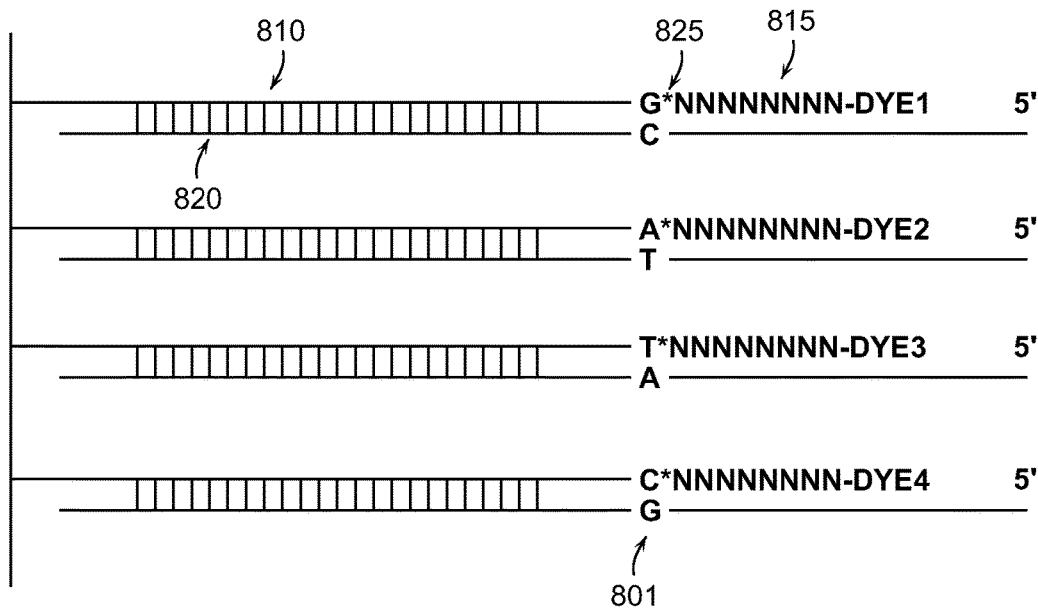
Figure 4C:
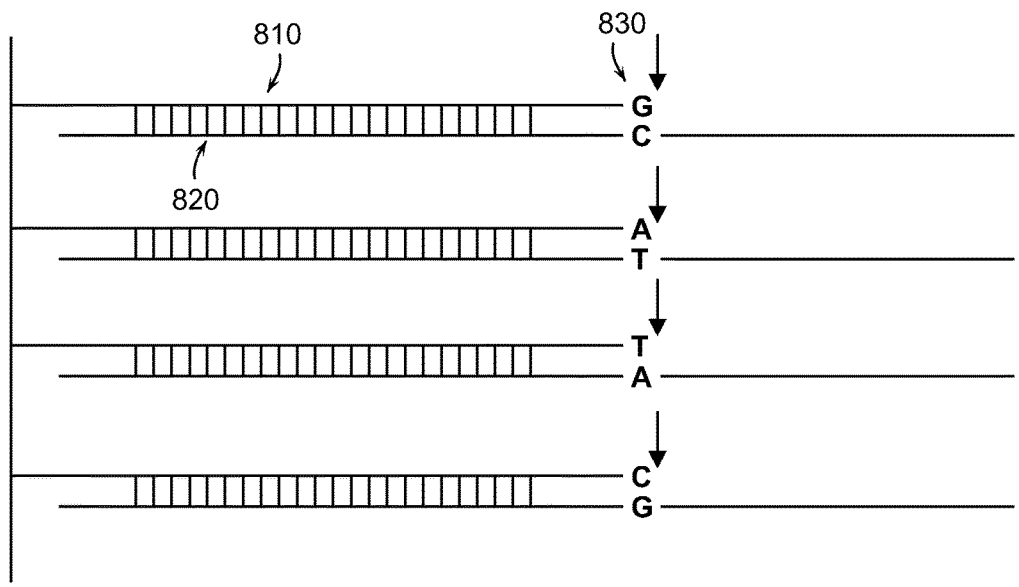
Figure 4D:
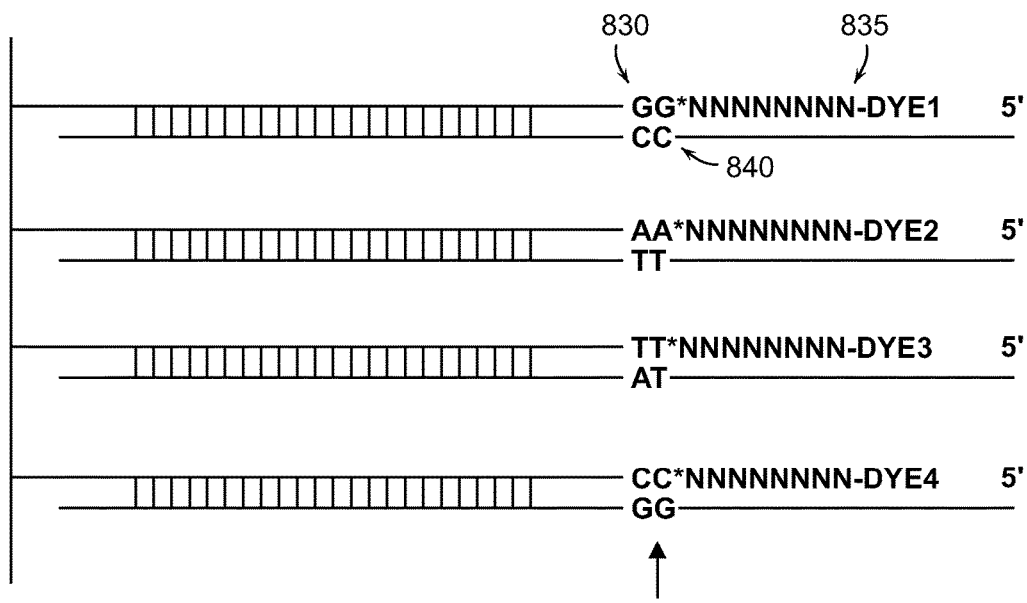

FIG. 3 shows a method of performing ALA using two color detection. FIG. 3A shows interrogation probes labeled with either Biotin or Fam (fluorescein) depending on the 3' terminal base of the interrogation probe. As shown, probes terminating with W where W is A or T have 5' biotin and probes terminating with S where S is G or C have 5'Fam. This method allows detection of S to W or W to S transitions which accounts for about 86% of known SNPs. A two color scan can be performed as follows. Biotin is first stained with streptavidin-cychrome, then biotinylated goat anti-streptavidin, then streptavidin-cychrome. The emission peak is 667 so a 680/50 nM bandwidth filter may be used for scanning. Fluorescein (Fam) is first stained with Rabbit anti-FL PE, then goat anti-rabbit FL conjugate then again with rabbit anti-Fl PE. The emission peak is 578 and a bandwidth filter of 580/50 nM may be used. FIG. 3B shows how two array probes may be used to interrogate a SNP. The SNP 701 has two alleles T or G and is shown as an AT base pair on the left or a GC base pair on the right. There are two array probes 710 and 720 for the SNP, one for each strand. Each array probe terminates just before the SNP on one of the strands. When the AT base pair is present the interrogation probe that terminates with an A and the interrogation probe that terminates with a T can be ligated to 710 and 720 respectively. When the GC base pair is present the interrogation probe that terminates with a C and the interrogation probe that terminates with a G can be ligated to 710 and 720 respectively.

In preferred aspects a two color array based ligation approach may be used to genotype more than 85% of human SNPs. Arrays may be synthesized with more than 1, 3, 5, or 10 million different probes on a 1.28 cm square array and smaller feature sizes are available. A SNP may be interrogated with a single probe, although two probes (one for each strand), provides more robust data. Smaller feature sizes allow larger numbers of different probes to be included on a single array of fixed size. This methodology could be used to genotype more than 2, 5, or 10 million SNPs simultaneously.

FIG. 4 illustrates a method for using cleavable ligation probes to sequence a plurality of bases in a target. In FIG. 4A the standard ligation approach is shown where the identity of the base at the interrogation position 801 is inferred from the color of the solution probe ligated to the array probe. The four different solution probes are each labeled with a different dye. The array probe 810 is ligated to the solution probe 815 after formation of a complex with the hybridized target 820. FIG. 4B shows a variation where the solution probe has a cleavage site 825 just 5' of the 3' terminal base. The cleavage site may be, for example, a photocleavable spacer, an abasic site or an RNA base. As shown in FIG. 4C, cleavage at the cleavage site releases the dye and all but one ligated base. The ligated base 830 is now attached to the array probe 810. Preferably a 5' phosphate group is generated. As shown in FIG. 4D, a second round of solution probes 835 can then hybridize immediately adjacent to 830 and provide information about the identity of a second interrogation position 840. Iterative cycles of CLT ligation, scanning and cleavage can be used to obtain sequence information about the hybridized target. In preferred aspects 15 to 25 rounds of CLT are used. The method may be used to sequence targets.

Figure 5A:
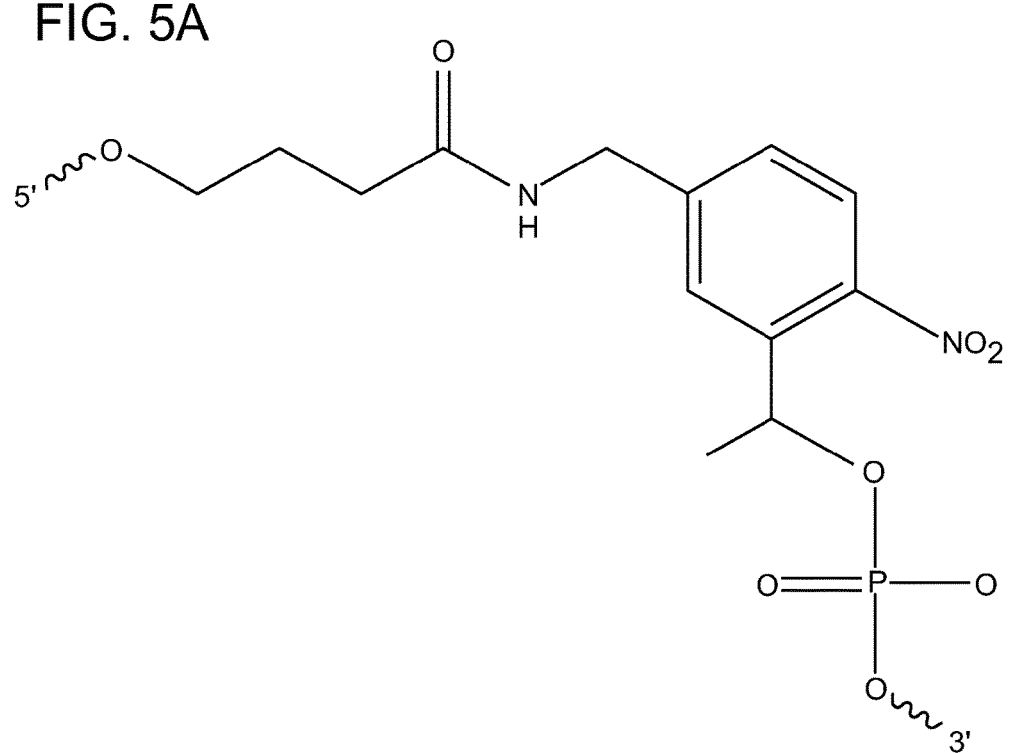
FIG. 5 shows examples of cleavable linkers.
Figure 5B:
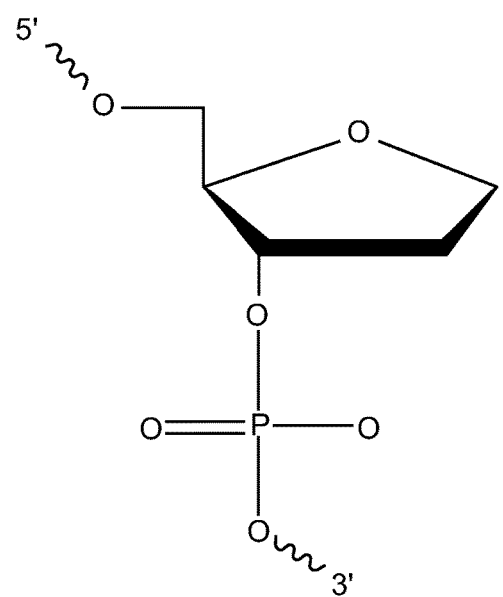

FIG. 5 shows examples of cleavable spacers. FIG. 5A is a photocleavable spacer. Cleavage can be performed by exposure to 300-365 nm light to result in a 5' phosphate. FIG. 5B shows the structure of a 1',2'-Dideoxyribose abasic spacer. Cleavage can be performed by the action of an enzyme such as Endonuclease V from E. coli to leave a 5' phosphate base. RNA bases can be cleaved by RNase H treatment of the duplex DNA. This also results in a 5' phosphate group capable participating in iterative cycles of ligation.

In some aspects conditions for ligation may be varied. Different array chemistries may be used including NNPOC, MeNPOC, BisB and LDS. Different probe lengths from 21 bases to 70 bases have been used. The target mass used in the hybridization may be varied. In some aspects the complexity of the sample is reduced before hybridization. In other aspects the whole genome may be hybridized with or without amplification. Hybridization time of the complex sample to the array may be varied, for example, from 8 hours to 2 to 3 days. The temperature of hybridization may be varied and different additives may be included, for example, yeast RNA or formamide. During the ligation reaction different enzymes may be used, for example, T4 DNA ligase, E. coli DNA ligase, Taq DNA ligase or T4 RNA ligase. The ligation time may be varied form 15 min to overnight. The temperature may be from 10° C. to 45° C. or higher if a thermostable ligase is used. Additives that may be included during ligation include DMSO, spermidine, SSB, NaPyrophosphate and salt. Yeast RNA and 3' phosphate competitor oligos may be added during ligation as non-specific competitors.

Concentration of the interrogation (or solution) probe may be varied from about 2 μM to about 100 μM and the length may be from about 6 to about 11. In some aspects the interrogation probe may contain one or more modifications such as inosine, 5' nitroindol, locked nucleic acids (LNAs), and RNA bases. The position of the "fixed" base is preferably terminal, but may be penultimate or internal. In another aspect the ligation may be chemical, for example, CNBr or EDC.

High density genotyping arrays have recently been used to identify polymorphisms associated with disease. See, for example, Klein et al. *Science*, 1109557, 2005, Butcher et al., *Behav Genet.* 34(5), 549-55 (2004), Gissen et al., *Nat. Genet.* 36(4):400-4 (2004), and Puffenberger et al *PNAS* 101:11689-94. High density genotyping arrays have also been used to identify regions of genomic amplification, deletion, loss of heterozygosity and allelic imbalance. See, for example, Cox, et al., *PNAS* 102:4542-47 (2005), Herr et al., *Genomics* 85(3):392-400 (2005), and Bignell et al., *Genome Res.* 14:287-95 (2004). The collection of probes may also be used as a semi-random representation of the entire genome. The array and collection of SNPs may be used for analysis of copy number, methylation, genetic rearrangements and to assess other genomic features.

EXAMPLES

Example 1. Array Ligation Assay with Base Specific Ligation

Start with a DNA sample containing pooled purified Chr4 PCR product at about 560 ng/μl. 120 μl Fragment. For each array to be hybridized 3.1 μl Purified PCR product @560 ng/ul, 2 μl Diluted Invitrogen DNase (1:186 dilution), 0.66 μl 10× Fragmentation Buffer, and 0.9 μl water were mixed, for a total of 6.66 μl per array with a DNA concentration of approximately 250 ng/uL. In this example a 40× reaction was set up with 124 μl purified PCR product, 80 μl diluted DNase, 26.4 μl 10× fragmentation buffer and 36 μl water. The reaction was then incubated at 37 C for 11 min, then 95 C for 10 min, and hold at 4 C.

As a control an aliquot of the fragmented DNA was end labeled with biotin prior to hybridization to the array. Labeling of the control was as follows: 12.5 μl fragmented DNA, 10 μl 5× buffer, 1.5 μl 30 mM DLR, 24 μl water, and 2 μl TdT were mixed for a total reaction volume of 50 μl. The reaction was incubated 20 min at 37 C then 5 min at 95 C. 44 μl water and 156 μl SR hyb were added to the reaction and the entire reaction was hybridized to an array.

Aliquots of the unlabeled fragmented DNA were hybridized to arrays with probes that are complementary to human genomic sequences [ENCODE regions]. The array used is the ENCODE 5' resequencing array, a modified version of the ENCODE array. For each 25 base region of the genomic sequence the array includes four probes that vary only at the 5' base. The probe sets are similar to resequencing probe sets, (for a description of resequencing arrays see, for example, Maitra et al., Genome Res. 14(5):812-9 (2004)). The arrays used in the present examples differ from standard resequencing arrays in the position of the interrogation position. Instead of having the variable position at the central position of the probe (position 13 of a 25 base probe) the variable position is at position 25 which is at the 5' end of the probe. Reactions were set up as follows: 62.5 μl of fragmented DNA was mixed with 407.5 μl water and 780 μl hybridization master mix (for 20.9 mLs mix 1320 μl 1.25M MES, 1430 μl 50×Denhardt's Solution, 320 μl 0.5 M EDTA, 330 μl HSDNA (10 mg/ml), 220 μl of OCR, 330 μl Human Cot-1 DNA (1 mg/ml), 110 μl TWEEN 20 detergent (3%), 1430 μl DMSO, 1540 μl 5M TMACl). The mixture was hybridized to arrays in aliquots of 200 μl. Arrays were washed in 0.2× wash at 37° C. for 30 min. Wash A is 6×SSPE, 0.01% TWEEN 20 detergent and Wash B is 0.6×SSPE, 0.1% TWEEN 20 detergent. The following ligation mixture was added to each array: 20 μl 10× *E. coli* ligase buffer, 8 μl of the appropriate dilution of interrogation oligo mixture (for example, 8 μl of 500 μM stock was used for final of 20 μM), 3 μl 1M NaCl, 4 μl *E. coli* ligase and water to 200 μl. The ligation mixture was incubated with the array for 3.5 hrs at room temp on a rotator. The arrays were washed in TE at 37° C. for 15 min and then stained (1, 2, 1 at 10 min each) and scanned as previously described (see GENECHIP Mapping 500K Assay Manual, Rev. 3, Chapter 5). In addition to the labeled target control the following interrogation oligos were tested: (1) 5' bioTEG/N8G at 20 μM (Operon), (2) 5' bioTEG/N8G at 5 μM (Operon), (3) 5' bio/N8G at 20 μM (IDT), (4) 5' bio/N8n at 20 μM total (IDT), and (5) 5'TEGbio/N8n at 20 μM total (Operon).

As expected, the array hybridized with labeled target showed signal at most features, reflecting that target is hybridized to most features. The N8n is expected to generate signal at most features. The N8G is expected to generate signal at about 25% of the features.

Example 2

The starting DNA was mixed chromosome 4 long range PCR products fragmented as described above. The DNA was hybridized to the ENCODE 5' resequencing arrays and the arrays were washed as described in Example 1. For example, rinse with RT 0.2×, 0.2× wash 37° C. for 30 min.

Mix 20 μl of 10× *E. coli* ligase buffer, 8 μl of 500 μM interrogation probe solution, 3 μl 1M NaCl, 4 μl *E. coli* Ligase and H$_2$O to 200 μl. The basic conditions were as follows. Incubate at room tamp for 3.5 hours on rotator. Wash at 37° C. for 15 min in TE, stain 1, 2, 1 for 100 minutes each and scan. The following oligos were tested in separate reactions as interrogation probes: N$_8$A, N$_8$T, N$_8$C, N$_8$G with 10 min 0.2× wash instead of 30 min, N$_8$G with 2× salt during ligation and N$_8$G with 20 min ligation time instead of 3.5 hours (all oligos were purchased from IDT).

Table 1 shows a grid of the expected perfect match base in the interrogation probe (row 1) compared to the brightest base (column 1). As expected the brightest base is overwhelmingly the perfect match base.

TABLE 1

|  | A observed | C observed | G observed | T observed |
| --- | --- | --- | --- | --- |
| A expected | 64,804 | 918 | 1,661 | 317 |
| C expected | 409 | 31,142 | 1,030 | 245 |
| G expected | 527 | 594 | 31,279 | 428 |
| T expected | 1,770 | 1,737 | 3,506 | 60,618 |

Table 2 shows the percentage of times the correct or incorrect interrogation probe was ligated. When the expected base was A, G or C the correct base was ligated at least 94% of the time. When T was the expected base the correct incorporation happened just less than 90% of the time. The most common error was ligation of a G instead of a T (5.18%). A T for A substitution was the least common error (0.47%).

TABLE 2

|   | A | C | G | T |
|---|---|---|---|---|
| A | 95.72 | 1.36 | 2.45 | 0.47 |
| C | 1.25 | 94.87 | 3.147 | 0.75 |
| G | 1.61 | 1.81 | 95.28 | 1.30 |
| T | 2.62 | 2.57 | 5.18 | 89.63 |

Example 3

To test 5' to 3' synthesis a 5K Tag array was synthesized 5' to 3' (reverse to standard 3' to 5' synthesis). MeNPOC and LDS were used. The probes were 21 mers. A control hybridization was performed using biotin labeled border probes. The expected hybridization pattern was observed. To test extension on the array, hybridized border oligos were extended with ddUTP under varying conditions. Enzymes tested were Klenow exo- or Sequenase with low or high ddUTP and low or high enzyme concentration. Reactions were at 37° C. The following parameters were also varied as follows: reaction temp from 37° C. to 50° C., DMSO denaturant from 0 to 1-%, start and kill reaction at 50° C., single stranded binding protein included (T4 gen3e 32 or *E. coli* SSB), magnesium concentration from 0 to 3.5 mM, addition of 0.1 to 2.5 mM spermidine, addition of Na Pyrophosphate from 0.5 to 12.5 mM, enzyme to ddNTP ratio and reaction time.

Example 4. Array Ligation Assay with 70 Base Probes and High Temperature Ligation To reduce background in the ALA reaction, thermostabile ligases and high temperature ligation conditions were compared to thermolabile ligases, e.g. T4 DNA ligase or *E. coli* DNA ligase, in combination with longer probes. Longer probes, for example, 30 to 70 bases permit the ligase reaction to be performed at higher temperatures, for example, 45 to 60° C. instead of the about 25° C. used for thermolabile ligases with 20 to 30 base probes. The higher temperature may be used to suppress background ligation from probe-probe self ligation or hairpin ligation.

The array used for the experiment was a "longmer" array having probes up to 70 bases. The surface is BisB and 214 synthesis steps were used to generate the probes of the array. The arrays were late building and edge optimized. All probes are tiled in triplicates as 5 based length increments from 25 bases to 70 bases. The SNP content is 1,000 random SNPs from the Affy 10K 2.0 array that meet the following criteria: in HapMap release 20, at least 70 bases from a repeat region, at least 70 bases from another SNP in dbSNP release 126, MAF greater than or equal to 0.05 in all three HapMap populations and excluded if the probes contain an XbaI restriction site. Tiling content was 3,000 base pairs from 384 plex amplicons in a defined set of kinase TACL probes (Faham et al.). Synthesis was BisB NNPOC 5' phosphate or BisB reverse NNPOC. Two different longer arrays were designed, 4c1 and 5c2. The following experiments used the 4c1 design.

To this array a control oligo, "Grid948 (70+15)" is hybridized. The Grid948 oligo is 85 bases long, 70 bases of which are complementary to a control probe present on the array in multiple locations. The oligo hybridizes to the control probe so that the remaining 15 bases forms a single stranded overhang available for hybridization of the labeled oligo, BioN8N for example. In this example, 500 nM Grid 948 (70+15) was hybridized to the longmer array for 5 min at RT and then the array was rinsed with water. Two thermostable DNA ligases, Pfu ligase or Taq ligase, were tested and compared to the standard low temperature reaction using *E. coli* ligase.

The reactions were as follows: reactions 1 and 2 contained 10 μl 10× pfu buffer, 20 μl BioN8N 125 μM each, 68 μl water, and 2 μl pfu ligase, reactions 3 and 4 contained 10 μl 10× taq ligase buffer, 20 μl BioN8N 125 μM each, 68 μl water, and 2 μl taq ligase and reaction 5 contained 10 μl 10× *E. coli* ligase buffer, 20 μl BioN8N 125 μM each, 68.5 μl water and 1.5 μl *E. coli* ligase. Reactions 1 and 3 were incubated at 45° C. for 30 minutes, reactions 2 and 4 were incubated at 60° C. for 30 minutes and reaction 5 was incubated at room temperature (~25° C.) for 30 minutes. The array was then washed for 10 min at 50° C. with TE and stained with SAPE using the standard 1, 2, 1 protocol. The arrays were scanned and the images analyzed. The control probes are arranged on the array to form a pattern that spells "Longmer 4c1" and the expected result from a successful reaction was labeling of the pattern on the array.

The results showed that Taq ligase worked well for ligation on the array at 45° C. and 60° C. with less background ligation at 60° C., but more "speckling". Pfu worked better at 45° C. than at 60° C. but the signal at 45° C. was still lower than the signal for Taq (at 45 or 60° C.) or *E. coli* ligase.

Example 5. Array Ligation Assay with Additives to Reduce Background

Different solution probe and salt concentrations were tested along with addition of different additives to identify conditions where the self-ligation background was reduced. The array was the longmer array used above with BisB 5' P synthesized in 214 steps. The hybridized oligo was again Grid948(70+15) but 1 nM was hybridized to the array in 6×SSPE for 30 min at 37° C. followed by washing in TE for 15 min at 42° C. The ligation reactions were set up as shown in Table 3.

TABLE 3

|   | 1 | 2 | 3 | 4 | 5 | 6 | 7 | 8 | 9 | 10 |
|---|---|---|---|---|---|---|---|---|---|---|
| 10x Taq Ligase buffer | 10 | 10 | 10 | 10 | 10 | 10 | 10 | 10 | 10 | 10 |
| BioN8N 500 μM | 20 | 10 | 2 | 20 | 20 | 20 | 20 | 20 | 20 | 20 |
| Yeast RNA |  |  |  |  |  |  |  |  | 12 |  |
| DMSO |  |  |  |  |  |  | 5 | 10 |  |  |
| 2M KCl |  |  |  |  | 10 | 15 |  |  |  |  |
| SSB |  |  |  | 3 |  |  |  |  |  |  |
| 180 mM ATP |  |  |  |  |  |  |  |  |  | 1 |
| water | 68 | 78 | 86 | 65 | 58 | 53 | 63 | 58 | 56 | 68 |
| 30 min at | 45° C. | 45° C. | 45° C. | 45° C. | 45° C. | 45° C. | 45° C. | 45° C. | 45° C. | 60° C. |

The reactions were incubated for 5 min at 45° C. then 2 µl Taq DNA ligase was added and the preheated mixture was then added to the preheated array and incubated for 30 min at the time shown in Table 3, last row. The arrays were then washed for 20 min at 50° C. in TE and stained using 1, 2, 1 SAPE.

Ligation of the BioN8N should only occur at the control probe features so signal should only be observed at those features. Any intensity observed from probes other than the control probes is background. The ratio of the mean intensity of all background to the mean control probe signal is the metric used to determine the extent of self-ligation (B/S ratio). Non-control probes of varying lengths are included on the array and B/S ratios were calculated for different length probes in the following lengths: 25, 30, 35, 40, 45, 50, 55, 60, 65, and 70.

In general, longer probes have higher B/S, ranging in the control (column 1) from 0.0695 for 25 mers to 0.153 for 70 mers and increasing by about 0.01 for every 5 bases added. Low solution probe concentration (column 2) and DMSO (columns 7 and 8) increased the B/S ratio. SSB (column 4) had a minimal effect on B/S. Addition of yeast RNA (column 9) increased the B/S relative to the control for 25, 30, 35 and 40 and decreased the B/S for 45, 50, 55, 60, 65 and 70 mers, but the variance from length to length was smaller, ranging from 0.0984 to 0.1054. Ultra low solution probe concentration (column 3) and high salt (columns 5 and 6) resulted in reduced the efficiency of the Taq ligation.

Example 6. Array Ligation Assay with Varied Hybridization Conditions

To optimize conditions for hybridization, salt, target concentration, ligase and wash stringency were varied. Short probes work well in the presence of tetraalkylammonium salts, but for longer probes sodium salts were tested. The DNA target mass was tested at two difference concentrations and a high stringency post hybridization wash was tested. Taq DNa ligase was also compared to *E. coli* DNA ligase. The hybridized target is whole genome DNA and arrays were scanned using 2 color scanning. The array used was again the longmer BisB 5'P 214 steps array described above. Different conditions tested are as shown in Table 4.

TABLE 4

|  | 1 | 2 | 3 | 4 | 5 | 6 | 7 | 8 |
|---|---|---|---|---|---|---|---|---|
| DNA | high | | | | low | | | |
| Hybe buffer | TMACl | TMACl | TMACl | NaCl | TMACl | TMACl | TMACl | NaCl |
| enzyme | *E. coli* | Taq | *E. coli* | *E. coli* | *E. coli* | Taq | *E. coli* | *E. coli* |
| Stringency wash | Std | Std | Ultra | Std | Std | Std | Ultra | Std |
| D7011 frag 8.4 µg/µl | 10 | 10 | 10 | 10 | 3 | 3 | 3 | 3 |
| Sr hyb buffer | 78 | 78 | 78 | | 78 | 78 | 78 | |
| 4X NaCl hyb | | | | 31.25 | | | | 31.25 |
| Grid948(70 + 15) 3'TdT biotin 100 nM | 1 | 1 | 1 | 1 | 1 | 1 | 1 | 1 |
| Formamide | 20 | 20 | 20 | 20 | 20 | 20 | 20 | 20 |
| water | 16 | 16 | 16 | 62.75 | 23 | 23 | 23 | 69.75 |

Set up the reactions as shown and incubate at 45° C. at 45 rpm overnight. Then wash and set up ligations on the array as shown in Table 5.

TABLE 5

|  | 1 | 2 | 3 | 4 | 5 | 6 | 7 | 8 |
|---|---|---|---|---|---|---|---|---|
| 0.2X SSPE 37° C. for 30 min | yes | yes | | yes | yes | yes | | yes |
| 0.1X SSPE 45° C. for 30 min | | | yes | | | | yes | |
| Ligation on array as follows: | | | | | | | | |
| 10x Taq buffer | | 10 | | | | 10 | | |
| 10X *E. coli* ligase buffer | 10 | | 10 | 10 | 10 | | 10 | 10 |
| 4X NaCl hyb | | | | 31.25 | | | | 31.25 |
| BioN8A | 5 | 5 | 5 | 5 | 5 | 5 | 5 | 5 |
| BioN8T | 5 | 5 | 5 | 5 | 5 | 5 | 5 | 5 |
| FamN8G | 5 | 5 | 5 | 5 | 5 | 5 | 5 | 5 |
| FamN8C | 5 | 5 | 5 | 5 | 5 | 5 | 5 | 5 |
| Water | 68.5 | 68.5 | 68.5 | 68.5 | 68.5 | 68.5 | 68.5 | 68.5 |
| Taq DNA ligase | | 1.5 | | | | 1.5 | | |
| *E. coli* ligase | 1.5 | | 1.5 | 1.5 | 1.5 | | 1.5 | 1.5 |
| incubation | RT 3 hr | 45 min at 45° C. | RT 3 hr | RT 3 hr | RT 3 hr | 45 min 45° C. | RT 3 hr | RT 3 hr |
| Wash 20 min TE 50° C. | | TE/5 mM EDTA/0.1% SDS | | | | | TE 5 mM EDTA/0/1% SDS | |

Stain 1, 2, 1, 2, 1 (15 min each) where the 1st stain is cychrome from Bd Science with α-Fl r-PE labeled Rabbit IgG A21250, 2nd stain is goat biotinylated α-SA (Vector) and Fl labeled goat α-rabbit F2765. Scan at 0.5 μm 590/680 nM 0.2 lazer 350 pmt. First scan at 590 and then at 680.

For each condition and each probe length (25, 30, 25, 40, 45, 50, 55, 60, 65, or 70) a metric was calculated based on the sum of the ratios from the average of all the signals from the expected color for that probe ligation to the signal from the other color. The results showed that a high DNA target mass is better than low DNA target mass, Taq ligase is better than *E. coli* ligase, standard stringency wash is better than ultra stringent wash and TMACl is better than NaCl. The highest ratio was observed for condition 2, High DNA, TMACl, Taq and standard stringency wash.

Example 7. Comparison of AMPLIGASE Thermostable DNA Ligase and Taq Ligase in Array Ligation Assay AMPLIGASE thermostable DNA ligase (EPICENTRE) is a high fidelity thermostable DNA ligase. The array is the longmer array with BisB 5' phosphate with 214 synthesis steps as described above. The hybridized target is whole genome DNA and the arrays are scanned for 2 colors. The target hybridization conditions are shown in Table 6.

TABLE 6

|  | 1 | 2 | 3 | 4 | 5 | 6 | 7 | 8 |
|---|---|---|---|---|---|---|---|---|
| 07011 frag 8.4 μg/μl | 20 | 20 | 20 | 20 | 20 | 20 | 20 | 20 |
| Sr hyb buffer | 78 | 78 | 78 | 78 | 78 | 78 | 78 | 78 |
| Grid948(70 + 15) 100 nM | 1 | 1 | 1 | 1 | 1 | 1 | 1 | 1 |
| Formamide | 20 | 20 | 20 | 20 | 20 | 20 | 20 | 20 |
| water | 6 | 6 | 6 | 6 | 6 | 6 | 6 | 0 |
| Yeast RNA 360 μg/μl | 0 | 0 | 0 | 0 | 0 | 0 | 0 | 6 |

Incubate at 45° C. at 60 rpm overnight and wash with 0.2×SSPE at 37° C. for 20 min. Then set up ligations on the arrays as shown in Table 7.

TABLE 7

|  | 1 | 2 | 3 | 4 | 5 | 6 | 7 | 8 |
|---|---|---|---|---|---|---|---|---|
| 10X Taq ligase buffer | 10 | 10 | 10 | 10 | 10 |  |  | 10 |
| 10X AMPLIGASE DNA Ligase buffer |  |  |  |  |  | 10 | 10 |  |
| BioN8A | 5 | 5 | 5 | 5 | 5 | 5 | 5 | 5 |
| BioN8T | 5 | 5 | 5 | 5 | 5 | 5 | 5 | 5 |
| FamN8G | 5 | 5 | 5 | 5 | 5 | 5 | 5 | 5 |
| FamN8C | 5 | 5 | 5 | 5 | 5 | 5 | 5 | 5 |
| Additives |  | 5 μl 2 M KCl | 12 μl yRNA |  |  |  |  |  |
| water | 67 | 62 | 55 | 67 | 67 | 67 | 67 | 67 |
| Taq DNA ligase | 3 | 3 | 3 | 3 | 3 |  |  | 3 |
| AMPLIGASE DNA Ligase |  |  |  |  |  | 3 | 3 |  |
| Incubation | 1 hr 45° C. | 1 hr 45° C. | 1 hr 45° C. | 2 hr 45° C. | 1 hr 60° C. | 1 hr 45° C. | 1 hr 60° C. | 1 hr 45° C. |

Wash with 0.2× wash for 5 min 0.1M NaOh, 6× rinse well. Stain 1,2,1,2,1, (10 min each). 1st stain is cychrome from Bd Science with α-Fl r-PE labeled Rabbit IgG A21250, 2nd stain is goat biotinylated α-SA (Vector) and Fl labeled goat α-rabbit F2765. Scan at 0.5 μm 590/680 nM 0.2 lazer 350 pmt. First scan at 590 and then at 680. Scanned images were evaluated for the intensity of the staining of the control probes (positive) relative to background. The results show that the addition of yRNA both during the hyb (column 8) and during the ligation (column 3) resulted in an improvement over the standard reaction (column 1). The yRNA may be occupying unhybridized probe sites and blocking self-ligation. AMPLIGASE thermostable DNA ligase at 45° C. (column 6) gave a higher signal to background than Taq (column 1) but lower intensities overall.

The effect of varying cell margins was also tested. AT 4c1 and 0.5 μm pixels, 3 different cell margins were tested, 4, 16 or 36 pixels. The results indicated that 4 pixels performed best, but all performed well.

Example 8. Effect of Different Length Interrogation Probes

In many of the previous examples a 9 mer interrogation probe or solution probe was used. To determine the effect of different interrogation probe lengths with longer array probes 9 mer, 10 mer and 11 mer interrogation probes were compared. The array was longmer 4c1 which is BisB 5' phosphate 214 step synthesis. 50 nM Grid948(70+15) probe was hybridized to the array for 5 min at room temp and rinsed with 0.2× wash. In this example, Betaine was also tested with the 9 mer as a possible DNA denaturing agent to reduce self-priming. Ligation reactions on the array were as shown in Table 8.

TABLE 8

|  | 1 | 2 | 3 | 4 | 5 | 6 |
|---|---|---|---|---|---|---|
| 10x Taq | 10 | 10 | 10 | 10 | 10 | 10 |
| 5M Betaine | 0 | 2 | 10 | 20 | 0 | 0 |
| 500 μM BioN8T | 5 | 5 | 5 | 5 |  |  |
| 500 μM BioN9T |  |  |  |  | 5 |  |
| 500 μM BioN10T |  |  |  |  |  | 5 |

TABLE 8-continued

|  | 1 | 2 | 3 | 4 | 5 | 6 |
|---|---|---|---|---|---|---|
| BSA | 1 | 1 | 1 | 1 | 1 | 1 |
| Water | 82 | 80 | 72 | 62 | 82 | 82 |
| Taq ligase | 2 | 2 | 2 | 2 | 2 | 2 |

Incubate at 45° C. for 30 min, rinse with TE, incubate for 5 min at RT with 0.1N NaOh, 6× rinse, SAPE stain 1, 2, 1. The results showed that background is higher with longer solution probes and that Betaine reduces background slightly.

Example 8. Array Ligation Assay with Variable Formamide

Different concentrations of formamide (8, 12, 16, or 20%) were tested to determine if the presence of denaturants reduces background. Two different concentrations of whole genome background target were also tested. The longer 4c1 array (BisB 5' P 214 step synthesis) described above was used. Target was hybridized as shown in Table 9.

TABLE 9

|  | 1 | 2 | 3 | 4 | 5 | 6 | 7 | 8 |
|---|---|---|---|---|---|---|---|---|
| D7011 frag 8.4 µg/µl | 20 | 20 | 20 | 20 | 10 | 10 | 10 | 10 |
| Sr hyb buffer | 78 | 78 | 78 | 78 | 78 | 78 | 78 | 78 |
| Grid948(70 + 15) 100 nM | 1 | 1 | 1 | 1 | 1 | 1 | 1 | 1 |
| Formamide | 10 | 15 | 20 | 25 | 10 | 15 | 20 | 25 |
| Water | 16 | 11 | 6 | 1 | 26 | 21 | 16 | 11 |

The arrays were incubated at 45° C. at 60 rpm overnight and washed with 0.2× wash for 30 min at 37° C. The ligations each had the following: 10 µl 10× Taq ligase buffer 5 µl each of BioN8A, BioN8T, FamN8G and FamN8C, 10 µl 5M Betaine, 57 µl water and 3 µl Taq DNA ligase. Ligations were incubated with the arrays for 1 hr at 45° C., rinsed with TE, washed for 5 min with 0.1M NaOH, 6×SSPE and rinsed well. The arrays were then stained 1, 2, 1, 2, 1 for 15 min each. The stains and scanning conditions were as in Example 7.

The results showed that higher denaturant concentrations favor longer probes as expected. A 12% concentration gave the highest signal to noise ratios and within that concentration the best signal to noise was observed at probe length 40 bases for both concentrations of whole genome target.

Example 9. Array Ligation Assay with Different Sources of Target

To test the sensitivity of the assay to different target prep methods unamplified whole genome target, fresh whole genome amplified (WGA) target and frozen WGA target were tested. The array was the longer 4c1 array described above. The targets were hybridized to the arrays as described above, each array also was hybridized with 1 µl 100 nM Grid948 oligo. Formamide was included in the hybridizations. The ligations were set up as follows: 10 µl 10× Taq ligase buffer, 5 µl each BioN8A, BioN8T, FamN8G, and FamN8C, 67 µl water and 3 µl Taq DNA ligase. Incubation was at 45° C. for 1 hr. Rinsing, staining and scanning was as in example 7. The results showed that frozen and fresh WGA targets work but not as well as unamplified.

What is claimed is:

1. A method for genotyping a plurality of target polymorphisms in a nucleic acid sample, the method comprising:

obtaining an array comprising a plurality of array locations wherein each array location comprises a plurality of array probes of the same sequence covalently attached to a solid support, wherein the array probes in an array location are perfectly complementary to the sequence that is immediately 5' of a target polymorphism in a target sequence, wherein said polymorphism is a single base change and wherein each array probe terminates at a base that is perfectly complementary to a first allele of said target polymorphism but not to a second allele of said target polymorphism, wherein said array also comprises a second array location comprising array probes that are perfectly complementary to the second allele;

hybridizing the nucleic acid sample to the array to allow array probes and target sequences to form complexes, wherein said complexes comprise a double stranded duplex region comprising a target sequence hybridized to an array probe and a single stranded region comprising target sequence, and washing to remove nucleic acid that is not hybridized specifically to an array location of the array;

adding a collection of labeled interrogation probes to the array to allow hybridization of the labeled interrogation probes to said single stranded region of said target sequences on the array, wherein said labeled interrogation probes are at least 6 bases in length and of random sequence;

adding a ligase to allow labeled interrogation probes to be ligated to the array probes in a template dependent manner;

washing the array to remove nucleic acids that are not covalently attached to the array;

detecting a hybridization pattern and determining from the hybridization pattern the presence or absence of labeled interrogation probe at array locations of the array and thereby determining the genotype of a plurality of target polymorphisms.

2. The method of claim 1 wherein the plurality of polymorphisms comprises single nucleotide polymorphisms, single base deletions and single base insertions.

3. The method of claim 1 wherein the labeled interrogation probes represent all possible sequences of 6 to 9 bases in length.

4. A method for genotyping a plurality of polymorphisms, wherein each of said plurality of polymorphisms is a single base change, the method comprising:

obtaining an array comprising a plurality of array locations wherein each array location comprises a plurality of array probes of the same sequence covalently attached to a solid support, wherein the sequence is perfectly complementary to the sequence that is immediately 5' of a target polymorphism and wherein each array probe terminates at a base immediately adjacent to a polymorphism;

hybridizing genomic DNA to be genotyped to the array wherein said genomic DNA hybridizes to complementary array probes to form a double stranded region and a single stranded 3' region of the genomic DNA;

washing to remove genomic DNA that is not hybridized specifically to an array location of the array;

adding a collection of labeled interrogation probes to the array to allow hybridization of the labeled interrogation probes to the single stranded 3' region of the genomic DNA wherein the labeled interrogation probes are differentially labeled depending on the base at the 3' end of each labeled interrogation probe, are at least 6 bases in length, and are of random sequence;

adding a ligase to allow the labeled interrogation probes to be ligated to the array probes in a template dependent manner;

washing the array to remove nucleic acids that are not covalently attached to the array;

detecting a hybridization pattern; and determining the genotype of a plurality of polymorphisms by determining the label or labels ligated to the array probes.

5. The method of claim 3 wherein the labeled interrogation probes represent all possible sequences of 6 to 9 bases in length.

6. A method for determining the genotype of a plurality of polymorphisms, wherein each of said plurality of polymorphisms is a single base change, the method comprising:

obtaining an array comprising at least 1,000,000 different target specific array probes wherein each target specific array probe is support bound at a different known or determinable location in the array, wherein each different target specific array probe is specific for one polymorphism in said plurality of polymorphisms and each different target specific array probe is specific for a different polymorphism in said plurality of polymorphisms;

hybridizing a target sample to the array to form complexes between the target specific array probes and complementary target sequences in the target sample, wherein said target sequences hybridize to complementary target specific array probes to form a double stranded region and a single stranded region of hybridized target sequence;

optionally removing unhybridized target sequences;

adding a plurality of labeled interrogation probes and a ligase to allow ligation of labeled interrogation probes to target specific array probes, wherein the labeled interrogation probes hybridize to the single stranded region of the hybridized target region immediately adjacent to the double stranded region, are at least 6 bases in length, are differentially labeled depending on the base at the 3' end of each labeled interrogation probe, and are of random sequence; and removing unligated labeled interrogation probes and determining the location of ligated labeled interrogation probes to determine the genotype of at least some of said plurality of polymorphisms.

7. The method of claim 6 wherein the labeled interrogation probes are a mixture of 5'-NNNNNNNNN-3' differentially labeled depending on the identity of the 3' base.

8. The method of claim 6 wherein the array comprises at least a first array probe and a second array probe for each polymorphism to be genotyped and wherein said first array probe and said second array probe are identical in sequence except at the base present at the 5' end of the array probe.

9. The method of claim 6 wherein for the array probes that are complementary to the target at a region that does not include the polymorphism but is immediately adjacent to the polymorphism, the labeled interrogation probe hybridizes to a region of the target that includes the polymorphism.

10. The method of claim 6 wherein the labeled interrogation probes represent all possible sequences of 6 to 9 bases in length.

* * * * *